US012569257B2

(12) United States Patent
    Xu

(10) Patent No.: US 12,569,257 B2
(45) Date of Patent: Mar. 10, 2026

(54) RADIAL ARTERY SMART COMPRESSION HEMOSTAT AND CONTROL METHOD THEREOF

(71) Applicant: The First Hospital of Jiaxing, Jiaxing (CN)

(72) Inventor: Haizhen Xu, Jiaxing (CN)

(73) Assignee: The First Hospital of Jiaxing, Jiaxing (CN)

( * ) Notice: Subject to any disclaimer, the term of this patent is extended or adjusted under 35 U.S.C. 154(b) by 328 days.

(21) Appl. No.: 18/388,544

(22) Filed: Nov. 10, 2023

(65) Prior Publication Data

US 2024/0156466 A1     May 16, 2024

(30) Foreign Application Priority Data

Nov. 11, 2022     (CN) .......................... 202211414529.9

(51) Int. Cl.
    *A61B 17/132*     (2006.01)
    *A61B 17/00*     (2006.01)
    (Continued)

(52) U.S. Cl.
    CPC .............................. *A61B 17/1325* (2013.01); *A61B 2017/00057* (2013.01); *A61B 2017/00075* (2013.01);
    (Continued)

(58) Field of Classification Search
    CPC ....... A61B 5/02; A61B 5/02042; A61B 5/021; A61B 5/02108; A61B 5/02116; A61B 5/02125; A61B 5/024; A61B 5/02438; A61B 5/02444; A61B 5/026; A61B 5/0261; A61B 17/132; A61B 17/1322; A61B 17/1325; A61B 17/1327; A61B 34/25; A61B 2034/252; A61B 2034/254;
    (Continued)

(56) References Cited

U.S. PATENT DOCUMENTS 5,119,824 A * 6/1992 Niwa ..................... A61B 5/025
                                                              606/34
5,307,811 A * 5/1994 Sigwart ................ A61B 17/132
                                                              600/490
(Continued)

OTHER PUBLICATIONS

Su et al. (CN 111743598 A) (Year: 2020).*

*Primary Examiner* — Kankindi Rwego
(74) *Attorney, Agent, or Firm* — Hemisphere Law, PLLC

(57)     ABSTRACT

A radial artery smart compression hemostat includes a housing, a pressure sensor, a gear motor and a compression rod. The pressure sensor and the gear motor are disposed in the housing. A fixed end of the pressure sensor is fixedly connected to the housing. The gear motor is fixedly disposed on a measuring end of the pressure sensor. An output end of the gear motor is threadedly connected to an end of the compression rod. A guiding channel is disposed on the housing and has the compression rod slidably disposed therein. A pressing plate is disposed on an end of the compression rod, exposed outside the housing, and has a compression pad detachably sleeved thereon. A bandage is disposed on the housing and used to tie the radial artery smart compression hemostat to a patient's wrist and thereby the compression pad is compressed on a radial artery puncture site.

10 Claims, 4 Drawing Sheets

(51) Int. Cl.

*A61B 17/12*      (2006.01)

*A61B 90/00*      (2016.01)

(52) U.S. Cl.

CPC ............... *A61B 2017/00084* (2013.01); *A61B 2017/00115* (2013.01); *A61B 2017/00398* (2013.01); *A61B 2017/00778* (2013.01); *A61B 2017/12004* (2013.01); *A61B 2090/064* (2016.02)

(58) Field of Classification Search

CPC ........ A61B 2034/256; A61B 2034/258; A61B 2090/064; A61B 2017/00057; A61B 2017/00075; A61B 2017/00084; A61B 2017/00115; A61B 2017/00398; A61B 2017/00778; A61B 2017/12004; A61F 5/30

USPC ........................................................ 606/203

See application file for complete search history.

(56) References Cited

U.S. PATENT DOCUMENTS

| | | | |
|---|---|---|---|
| 7,517,328 B2 * | 4/2009 | Hoffmann ............ | A61H 31/005 601/48 |
| 2008/0071202 A1 * | 3/2008 | Nardi ..................... | A61H 11/00 601/97 |
| 2010/0179586 A1 * | 7/2010 | Ward ................... | A61B 17/135 606/202 |
| 2014/0012120 A1 * | 1/2014 | Cohen ................ | A61B 5/02042 600/371 |
| 2015/0201948 A1 * | 7/2015 | Kornowski ........ | A61B 17/1355 606/203 |
| 2017/0215749 A1 * | 8/2017 | Zhuo .................. | A61B 5/02055 |
| 2019/0343536 A1 * | 11/2019 | Keene ................ | A61B 17/1355 |
| 2021/0068843 A1 * | 3/2021 | Takano .............. | A61B 17/1355 |
| 2022/0233254 A1 * | 7/2022 | Shelton, IV ....... | A61B 18/1442 |

\* cited by examiner

RADIAL ARTERY SMART COMPRESSION HEMOSTAT AND CONTROL METHOD THEREOF

CROSS-REFERENCE TO RELATED APPLICATION

This application claims priority to Chinese Patent Application No. 202211414529.9, filed on Nov. 11, 2022, the disclosure of which is incorporated herein by reference in its entirety.

TECHNICAL FIELD

The present disclosure relates to the field of radial artery hemostat technologies, and particularly to a radial artery smart compression hemostat and a control method thereof.

BACKGROUND

The world health organization (WHO) predicted that the harm of cardiovascular diseases will become the first, and China may usher in an "epidemic peak" of coronary heart diseases. The percutaneous transluminal coronary intervention (PCI) is currently one of the most widely used and most important treatments for coronary heart diseases, and it is also a preferred method recommended by guidelines for treatments of ST-segment elevation myocardial infarction (STEMI). Clinically, more than 90% of percutaneous coronary interventions are achieved through a radial artery puncture approach, and hemostasis at a radial artery puncture site, as an important part of this diagnosis and treatment, is directly related to prognoses of patients. At present, there are two compression hemostasis methods for clinical radial artery puncture sites. A first method is that, a self-made elastic bandage is used to locally compress and bandage the puncture site to stop bleeding, but this method cannot adjust tightness and thus affects venous reflux of the hand, thereby causing pain, swelling and numbness of the limb of the patient, so that complications such as skin damage, forearm hematoma, osteofascial syndrome or the like would occur; and in severe cases, it even causes occlusion of blood vessels of the operated limb, a risk of occurrence of postoperative complications is increased. A second method is that, a special radial artery hemostat is used to locally compress the puncture site for hemostasis, and there are two types of radial artery hemostats, i.e., balloon type and spiral type, are commonly used in clinic. A compression balloon of the balloon type radial artery hemostat is spherical, and when being used in a large area of compression, it is difficult to accurately and effectively compress the puncture site. For the spiral type radial artery hemostat, it is difficult to control and monitor a force of rotary compression, which can easily lead to blood oozes out from the radial artery into a subcutaneous area, and it is not easy to detect early, leading to the occurrence of complication of forearm swelling.

Regarding the use of the self-made elastic bandage or the special radial artery hemostat on the wrist to compress the radial artery puncture site for hemostasis, doctors often rely on experiences to determine degrees of bandage tightness at the beginning and during the whole decompression process, and a local compression force of the radial artery hemostat applied on the puncture site, which has the risk of occurrence of complications caused by too high or too low pressure. At present, because the special radial artery hemostat belongs to consumables, a high device cost has brought a certain economic burden to patients. Therefore, while reducing the cost of medical consumables, how to scientifically, accurately and effectively compress the radial artery puncture site for hemostasis, thereby reduce occurrence of complications, reduce medical care costs, reduce pain of patients, and improve patient's medical experiences is of great clinical value for the research and development of radial artery hemostats.

SUMMARY

In order to solve the problems that the radial artery hemostat in the related art when compresses the puncture site has low compression precision, is easy to cause compression ischemia, and causes oozing of blood due to insufficient pressure, embodiments of the present disclosure provide a radial artery smart compression hemostat and a control method thereof.

To solve the above technical problems, the present disclosure proposes technical solutions as follows. Specifically, a radial artery smart compression hemostat includes: a housing, a pressure sensor, a gear motor, and a compression rod; the pressure sensor and the gear motor both are disposed in the housing, a fixed end of the pressure sensor is fixedly connected to the housing, the gear motor is fixedly disposed on a measuring end of the pressure sensor, an output end of the gear motor is threadedly connected to an end of the compression rod, a guiding channel is disposed on the housing, the compression rod is slidably disposed in the guiding channel, a pressing plate is disposed on an end of the compression rod facing away from the gear motor, the pressing plate is exposed outside the housing, a silicone compression pad is detachably sleeved on the pressing plate, a bandage is disposed on the housing, the bandage is configured (i.e., structured and arranged) to tie the radial artery smart compression hemostat to a wrist of a patient and thereby the compression pad is compressed on a radial artery puncture site.

In some embodiments, the pressing plate is rectangular, and a lengthwise direction of the pressing plate is oriented along a blood vessel direction of a radial artery. Since a skin puncture site and a blood vessel puncture site at the radial artery puncture site do not coincide with each other, they are generally distributed in two places along the blood vessel direction of the radial artery. Anyway, as long as a center location of the pressing plate in the lengthwise direction of the pressing plate is approximately aligned with the blood vessel puncture site, it can effectively prevent the radial artery from oozing of blood to a subcutaneous area caused by a deviation of compression site, thereby ensure accurate and effective compression hemostasis at the radial artery puncture site, and the compression pad can be well fitted with the skin to improve comfort.

In some embodiments, two vibration sensors are disposed on the pressing plate, and the two vibration sensors are respectively arranged on a proximal end and a distal end of the radial artery puncture site. The two vibration sensors are respectively configured to monitor a pulse intensity at the proximal end and a pulse intensity at the distal end. According to a pulse vibration amplitude difference between the pulse intensity at the proximal end and the pulse intensity at the distal end, a blood flow patency (or occlusion) condition at the distal end can be determined, based on which a pressure of the compression pad can be adjusted.

In some embodiments, far-infrared temperature sensors are disposed on the pressing plate and arranged along the lengthwise direction of the pressing plate, and the far-infrared temperature sensors are located between the two vibration sensors. According to temperatures returned by the far-infrared temperature sensors, it can be determined whether there is oozing of blood and a size of the oozing of blood, based on which the pressure of the compression pad can be adjusted. In general, a skin surface temperature at the puncture site is lower than the body temperature, and maintains at a relatively stable temperature value; if oozing of blood occurs, blood oozes out from the blood vessel into the skin at the puncture site, the temperature at the puncture site rises to a certain extent; if the blood oozes out continuously, the temperature rises continuously and is close to the body temperature; if the oozing of blood is temporary, after the temperature rises, the temperature will gradually stabilize and approach the initial skin temperature.

In some embodiments, a display screen and keys are disposed on the housing, an integrated circuit board and a battery are disposed in the housing; the integrated circuit board is disposed thereon a controller, an alarm loudspeaker, a clock chip, and wireless charging coil; the gear motor, the pressure sensor, the display screen, the keys, the controller, the alarm loudspeaker, the clock chip, the wireless charging coil and the battery all are electrically connected to the integrated circuit board; the two vibration sensors and the far-infrared temperature sensors are electrically connected to the integrated circuit board through a flexible flat cable (FFC); the flexible flat cable is arranged passing through the pressing plate and the compression rod sequentially; and the wireless charging coil is configured to charge the battery. The circuit layout is reasonable and reliable, and is convenient to control and operate, and the wireless charging coil can charge the battery safely and conveniently.

In some embodiments, the pressure sensor is a stress-strain pressure sensor, a fixing plate is disposed between the fixed end of the pressure sensor and the housing, the fixed end of the pressure sensor and the housing are fixedly connected to the fixing plate through screws, and the gear motor is fixedly disposed on the measuring end of the pressure sensor through a connecting piece. The gear motor can drive the compression rod, the pressing plate and the compression pad sequentially to move close to or away from the radial artery puncture site, a pressure received by the compression pad in contact with the radial artery puncture site is transmitted to the pressure sensor through the pressing plate, the compression rod and the gear motor sequentially, so that the pressure sensor can acquire the pressure. Therefore, the pressure acquired by the pressure sensor is a pressure to which the entire compression pad is subjected, i.e., a pressure applied by the compression pad to the skin at the radial artery puncture site, and thus the overall measurement is more accurate.

In another aspect, a control method of the radial artery smart compression hemostat according to any one of the above embodiments includes steps of:

S1, recording a systolic blood pressure as Ps and a diastolic blood pressure as Pd of a patient measured before an operation;

S2, tying the radial artery smart compression hemostat to a wrist of the patient through the bandage after the operation, wherein a center location of the compression pad abuts against the radial artery puncture site; and S3, driving the compression rod, the pressing plate and the compression pad sequentially through the gear motor to move close to the radial artery puncture site, thereby making the compression pad apply a pressure force F to skin at the radial artery puncture site; converting the pressure force F into a pressure intensity P correspondingly; setting a high-pressure compression time $\Delta T0$, a high-pressure relief time $\Delta T1$, various stage compression times $\Delta Tj$, and a total compression time Tt, where $Tt=\Delta T0+\Delta T1+\Delta Tj*n$; wherein at a beginning of hemostasis, $P=Ps+Pa1$ and lasts for $\Delta T0$; P then gradually decreases at a rate of $Pa1/\Delta T1$, until $P=Ps$; and afterwards, P decreases gradually with the stage compression times $\Delta Tj$, $P=Ps-(Ps-Pd+Pa2)*j/n$, until $P=Pd-Pa2$, and a process of hemostasis is ended; where Pa1 and Pa2 both are constants and each correspond to a threshold, $j=1, 2, 3, \ldots, n$, and n is an integer.

In some embodiments, the pressing plate is rectangular, and a lengthwise direction of the pressing plate is orientated along a blood vessel direction of a radial artery; two vibration sensors are disposed on the pressing plate, and the two vibration sensors are respectively arranged on a proximal end and a distal end of the radial artery puncture site; and far-infrared temperature sensors are disposed on the pressing plate and arranged along the lengthwise direction of the pressing plate, and the far-infrared temperature sensors are located between the two vibration sensors;

the S3 includes: recording a pulse intensity at the proximal end as Ha1 and a pulse intensity at the distal end as Ha2 measured by the two vibration sensors respectively; setting a pulse vibration amplitude difference coefficient as $ha=Ha2/Ha1$, wherein a value of ha in a range of 0 to 02 indicates a blood vessel is occluded and there is no blood flow at the distal end, and the value of ha in a range of 0.8 to 1 indicates the blood vessel is unobstructed; recording a skin surface temperature at the radial artery puncture site measured by the far-infrared temperature sensors as Temp, recording the skin surface temperature at the radial artery puncture site as Temp0 when there is no oozing of blood at the radial artery puncture site, and recording the skin surface temperature at the radial artery puncture site as Temps after rises resulting from continuous oozing of blood when there is oozing of blood at the radial artery puncture site which causes the skin surface temperature at the radial artery puncture site rises, where $Temp0 \leq Temp \leq Temps$;

moreover, the control method includes: in a whole process of hemostasis, monitoring ha and Temp in real time; setting a blood vessel occlusion interval time Tc and a blood vessel release interval time To; releasing the pressure intensity until the value of ha is in a range of 0.45 to 0.55 when a time length of the value of ha being in the range of 0 to 0.2 is greater than the time Tc and maintaining for the time To, and then the compression pad restoring to the pressure intensity before the releasing; making the pressure intensity P return to immediately preceding pressure level and then be maintained for $\Delta Tj$ when Temp rises abnormally at any time during the whole process of hemostasis, determining whether $Temp \leq Temp0+0.5$ or not within a time period of $\alpha*\Delta Tj$ before current moment when current $\Delta Tj$ ends, going to a next pressure stage if $Temp \leq Temp0+0.5$, whereas if $Temp \leq Temp0+0.5$ is not satisfied, continuing maintaining current pressure stage for a time period of $\alpha*\Delta Tj$, where $\alpha$ is a constant and corresponds to a threshold. According to the difference of pulse vibration amplitudes returned by the two vibration sensors, the blood flow condition (patency or occlusion) at the distal end can be determined; according to the temperatures returned by the far-infrared temperature sensors, whether there is oozing of blood and a size of the oozing of blood can be determined; and then the pressure of the compression pad applied on the radial artery puncture site can be adjusted in time, which can effectively avoid long-term compression ischemia at the distal end, effectively avoid oozing of blood caused by insufficient pressure, achieve the purpose of radial artery compression hemostasis as soon as possible under the condition of ensuring smooth blood flow of the operated limb to the greatest extent and no or less oozing of blood, and reduce secondary injury and sequelae after compression.

In some embodiments, a value range of Pa1 is 0 to 30 millimeters of mercury (mmHg), a value range of Pa2 is 0 to 20 mmHg, and a value range of α is 0 to 0.5. The value of Pa1 is comprehensively determined by a use condition of anticoagulant, a condition of blood pressure and a condition of coagulation function of the patient. The pressure applied onto the radial artery puncture site is set according to individual conditions of patients, so that the pressure applied to the radial artery puncture site by the compression pad can be ensured to be moderate, long-term compression ischemia at the distal end can be effectively avoided, oozing of blood caused by insufficient pressure can be also effectively avoided, and thus hemostatic effect of compression hemostasis can be ensured consequently.

In some embodiments, the radial artery smart compression hemostat is disposed with an alarm loudspeaker, and the control method further includes: S4, promoting by the alarm loudspeaker, to indicate that the radial artery smart compression hemostat needs to be removed from the wrist of the patient, thereby ensuring that a medical staff ends the hemostasis operation for the patient in time.

Embodiments of the present disclosure may achieve one or more of beneficial effects as follows.

1. For the radial artery smart compression hemostat according to the present disclosure, the gear motor drives the compression rod, the pressing plate and the compression pad sequentially to move close to or away from the radial artery puncture site, a pressure received by the compression pad in contact with the radial artery puncture site is transmitted to the pressure sensor through the pressing plate, the compression rod and the gear motor sequentially, so that the pressure sensor can acquire the pressure. Therefore, the pressure acquired by the pressure sensor is a pressure to which the entire compression pad is subjected, i.e., a pressure applied by the compression pad to the skin at the radial artery puncture site, and thus the overall measurement is more accurate.

2. For the radial artery smart compression hemostat according to the present disclosure, the pressure applied to the radial artery puncture site can be set according to individual blood pressures of patients, and a rule of decompression time-pressure is preset, automatic decompression is carried out in use according to the setting, manual intervention can be also carried out to stop decompression, and the pressure can be read on the display screen in real time. In the decompression process, the pulse intensities and the blood oozing condition are monitored in real time, and cases of blood vessel occlusion for an excessively long time and occurrence of oozing of blood can be automatically processed, which can effectively avoid long-term compression ischemia at the distal end, effectively avoid oozing of blood caused by insufficient pressure, achieve the purpose of radial artery compression hemostasis as soon as possible under the condition of ensuring smooth blood flow of the operated limb to the greatest extent and no or less oozing of blood, and reduce secondary injury and sequelae after compression.

3. For the radial artery smart compression hemostat according to the present disclosure, its structure is simple and reliable, the design thereof is ingenious, the radial artery smart compression hemostat is worn on the assist of a medical staff to achieve compression hemostasis after an operation is finished, and after decompression and hemostasis are finished, the alarm loudspeaker can give an alarm sound to remind the medical staff to take down the hemostat in time, and thus the manipulation is very simple and convenient.

4. For the radial artery smart compression hemostat according to the present disclosure, it can be repeatedly used after being disinfected, and only the compression pad needs to be replaced; the compression pad contacted with the skin is a disposable consumable, so that the cost is low, and the radial artery smart compression hemostat is safe and convenient to use; and the hemostat is low in material cost, so that an economic burden of the patient can be greatly reduced, a basis is provided for popularization and application of the radial artery intelligent compression hemostat in a wider range, and further achievement transformation can be realized.

BRIEF DESCRIPTION OF DRAWINGS

In order to more clearly illustrate technical solutions in embodiments of the present disclosure, accompanying drawings used in the embodiments will be briefly introduced below. Apparently, the accompanying drawings in the following description are only some embodiments of the present disclosure, and for those skilled in the art, other drawings can be obtained according to these illustrated drawings without creative work.

Figure 1:
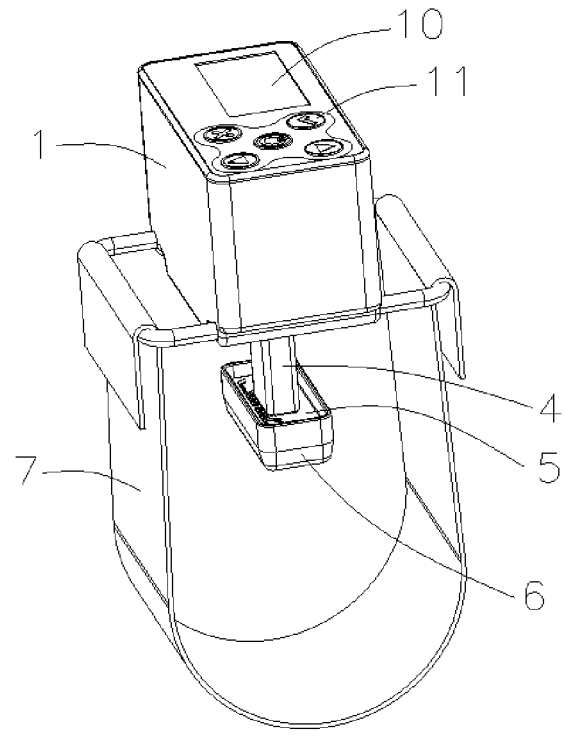
FIG. 1 illustrates a schematic perspective structural view of a radial artery smart compression hemostat according to an embodiment of the present disclosure.

In the drawings: 1, housing; 1-1, guiding channel; 2, pressure sensor; 3, gear motor; 4, compression rod; 5, pressing plate; 6, compression pad; 7, bandage; 8, vibration sensor; 9, far-infrared temperature sensor; 10, display screen; 11, key; 12, integrated circuit board; 13, battery; 14, controller; 15, alarm loudspeaker; 16, clock chip; 17, wireless charging coil; 18, flexible flat cable; 19, fixing plate; 20, connecting piece; 21, wrist.

DETAILED DESCRIPTION OF EMBODIMENTS

In the following, technical solutions of embodiments of the present disclosure will be clearly and completely described with reference to the accompanying drawings of the embodiments of the present disclosure. Apparently, the described embodiments are only some of embodiments of the present disclosure, not all of embodiments of the present disclosure. The following description of at least one exemplary embodiment is merely illustrative in nature and is in no way intended to limit the present disclosure and its application or uses. Based on the described embodiments of the present disclosure, all other embodiments obtained by those skilled in the art without creative work are within the scope of protection of the present disclosure.

Referring to FIG. 1 through FIG. 6, a radial artery smart compression hemostat includes: a housing 1, a pressure sensor 2, a gear motor 3 and a compression rod (also referred to as compression bar) 4. The pressure sensor 2 and the gear motor 3 both are arranged in the housing 1. A fixed end of the pressure sensor 2 is fixedly connected to the housing 1. The gear motor 3 is fixedly disposed on a measuring end of the pressure sensor 2. An output end of the gear motor 3 is threadedly connected to an end of the compression rod 4. In an illustrated embodiment, the gear motor 3 is a miniature gear motor. The housing 1 is disposed with a guiding channel 1-1, and the compression rod 4 is slidably disposed in the guiding channel 1-1. An end of the compression rod 4 facing away from the gear motor 3 is disposed with a pressing plate 5. The pressing plate 5 is exposed outside the housing 1. A transparent silicone compression pad 6 is detachably sleeved on the pressing plate 5. A bandage 7 is disposed on the housing 1. The bandage 7 is configured (i.e., structured and arranged) to tie the radial artery smart compression hemostat to a wrist 21 of a patient, and in this situation, the compression pad 6 compresses a radial artery puncture site. The compression pad 6 is a disposable consumable, is safe and sanitary, is convenient to replace, and is low in cost.

Since a skin puncture site and a blood vessel puncture site at the radial artery puncture site do not coincide with each other, they are generally distributed in two places along a blood vessel direction of a radial artery. In an illustrated embodiment, the pressing plate 5 is rectangular in shape, as shown in FIG. 1, FIG. 2, FIG. 3 and FIG. 5, a lengthwise direction of the pressing plate 5 is oriented along a direction of a blood vessel of the radial artery, as long as a center location thereof in the lengthwise direction of the pressing plate 5 is approximately aligned with the blood vessel puncture site, it can effectively prevent the radial artery from oozing of blood into a subcutaneous area caused by a deviation of compression site, thereby ensure accurate and effective compression hemostasis at the radial artery puncture site, and the compression pad 6 can be well fitted with the skin to improve comfort.

Figure 2:
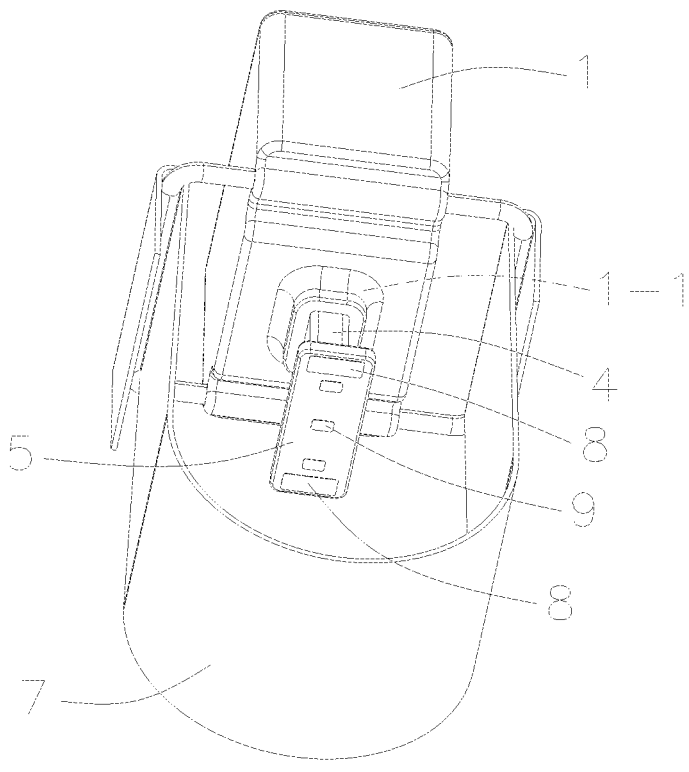
FIG. 2 illustrates another schematic perspective structural view of the radial artery smart compression hemostat according to an embodiment of the present disclosure, where a compression pad thereof is removed.
Figure 3:
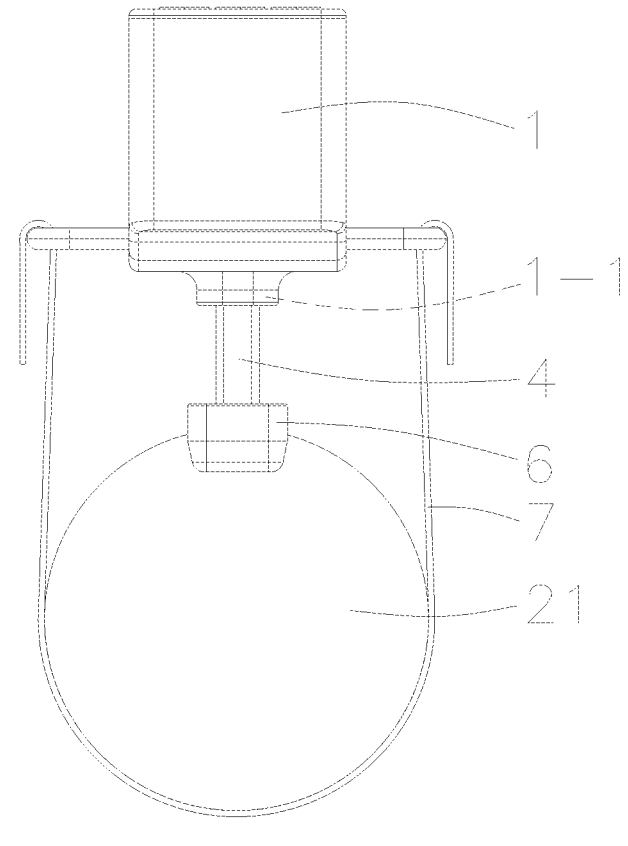
FIG. 3 illustrates a schematic front view of the radial artery smart compression hemostat according to an embodiment of the present disclosure.
Figure 4:
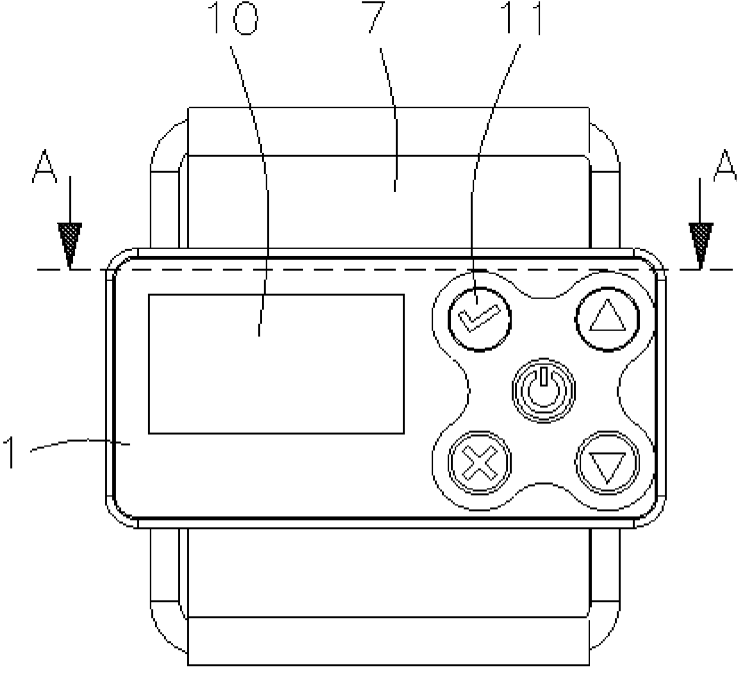
FIG. 4 illustrates a schematic top view of the radial artery smart compression hemostat according to an embodiment of the present disclosure.
Figure 5:
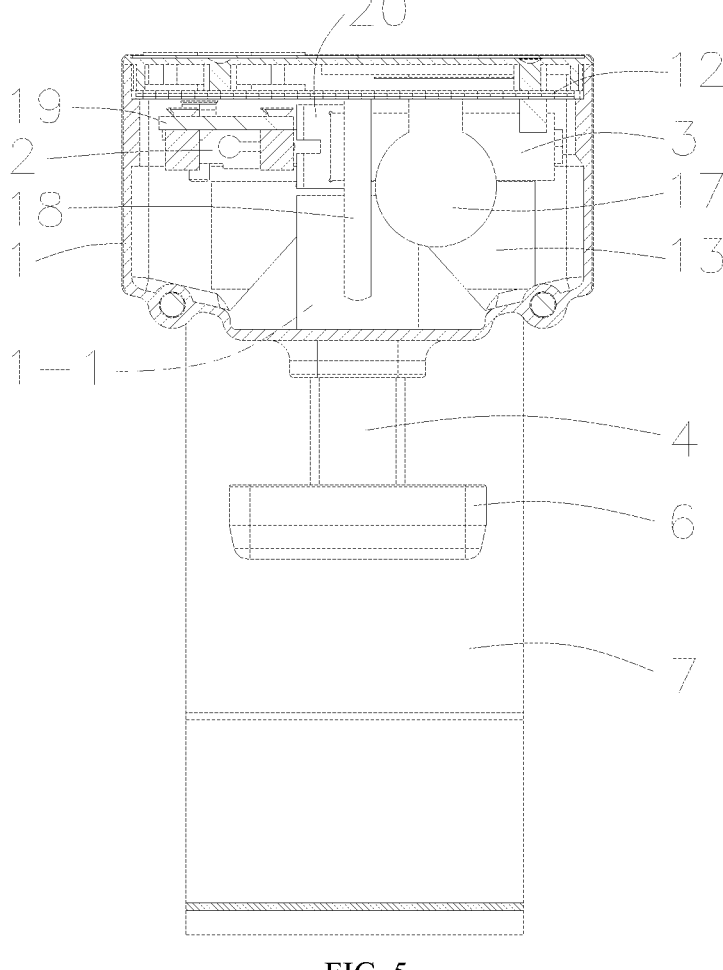
FIG. 5 illustrates a schematic cross-sectional view taken along the direction A-A in FIG. 4.
Figure 6:
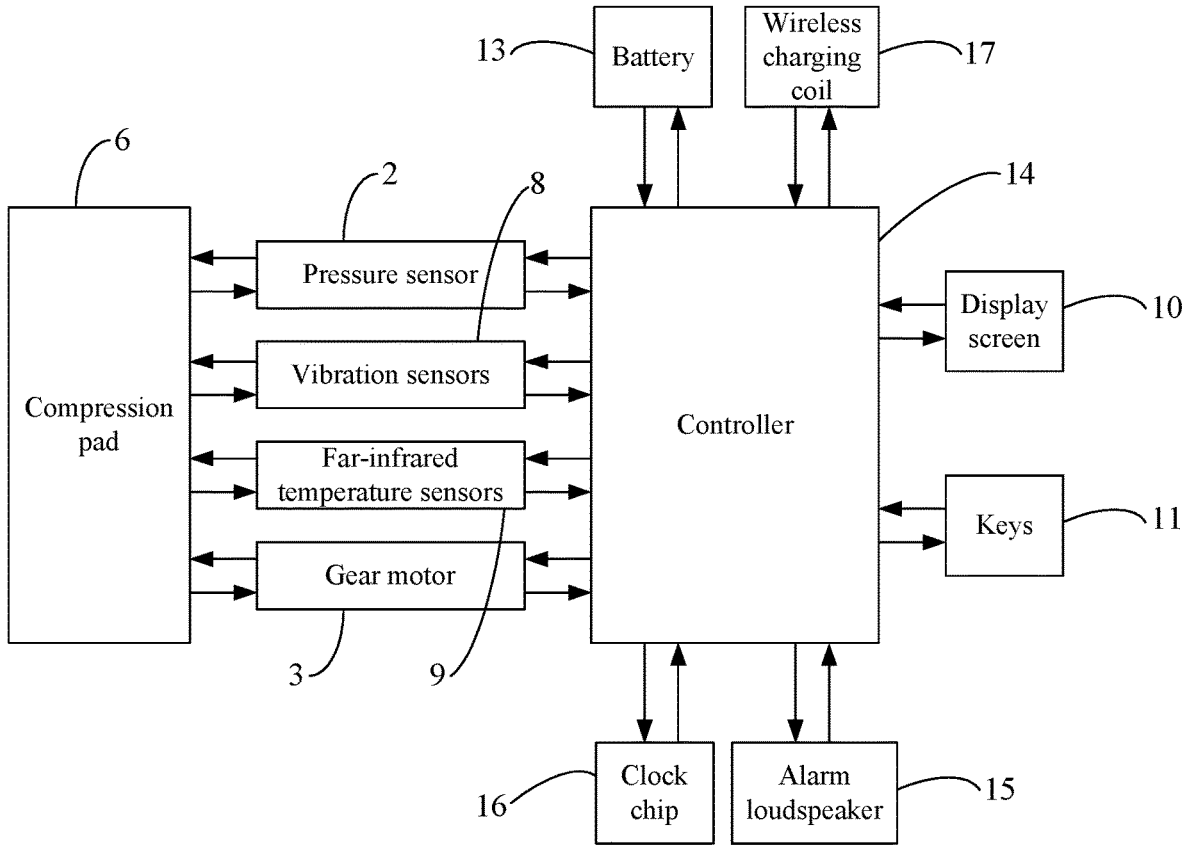
FIG. 6 illustrates a schematic control principle diagram of the radial artery smart compression hemostat according to an embodiment of the present disclosure.

In order to effectively prevent compression ischemia at a distal end for an excessive long time, to effectively prevent oozing of blood due to insufficient pressure, and to monitor whether there is oozing of blood and a size of the oozing of blood in real time, in an illustrated embodiment, as shown in FIG. 2, FIG. 5 and FIG. 6, two vibration sensors 8 are disposed on the pressing plate 5. Each of the vibration sensors 8 is, for example, a polyvinylidene fluoride (PVDF) vibration sensor. The two vibration sensors 8 are arranged on a proximal end and the distal end of the radial artery puncture site, respectively. The two vibration sensors 8 are respectively configured to monitor a pulse intensity at the proximal end and a pulse intensity at the distal end. According to a pulse vibration amplitude difference between the pulse intensity at the proximal end and the pulse intensity at the distal end, a blood flow patency (or occlusion) condition at the distal end can be determined, based on which a pressure of the compression pad 6 can be adjusted correspondingly. As illustrated in FIG. 2, FIG. 5 and FIG. 6, multiple (i.e., more than one) far-infrared temperature sensors 9 are arranged on the pressing plate 5 along the lengthwise direction of the pressing plate 5, and the far-infrared temperature sensors 9 are located between the two vibration sensors 8. According to temperatures returned by the far-infrared temperature sensors 9, it can be determined whether there is oozing of blood and a size of the oozing of blood (measured by cooperation of the far-infrared temperature sensors 9), based on which the pressure of the compression pad 6 can be adjusted correspondingly. In general, a skin surface temperature at the puncture site is lower than the body temperature, and maintains at a relatively stable temperature value; if blood oozes out from the blood vessel to the skin at the puncture site, the temperature at the puncture site rises to a certain extent; if the blood oozes out continuously, the temperature rises continuously and is close to the body temperature; if the oozing is temporary, after the temperature rises, the temperature will gradually stabilize and approach the initial skin temperature.

In order to ensure that the pressure sensor 2 can accurately measure a pressure applied to the skin by the compression pad 6, in an illustrated embodiment, the pressure sensor 2 is a stress-strain pressure sensor, specifically an aluminum metal stress-strain pressure sensor. As shown in FIG. 5, a fixing plate 19 is disposed between the fixed end of the pressure sensor 2 and the housing 1, and the fixed end of the pressure sensor 2 and the housing 1 both are fixedly connected with the fixing plate 19 through screws. The gear motor 3 is fixedly disposed on the measuring end of the pressure sensor 2 through a connecting piece 20. The gear motor 3 is configured to drive the compression rod 4, the pressing plate 5 and the compression pad 6 sequentially to move close to or away from the radial artery puncture site, a pressure received by the compression pad 6 in contact with the radial artery puncture site is transmitted to the pressure sensor 2 through the pressing plate 5, the compression rod 4 and the gear motor 3 sequentially, so that the pressure sensor 2 can acquire the pressure. Therefore, the pressure acquired by the pressure sensor 2 is a pressure to which the entire compression pad 6 is subjected, i.e., a pressure applied by the compression pad 6 to the skin at the radial artery puncture site, and thus the overall measurement is more accurate.

In order to ensure reliable and convenient use of the radial artery smart compression hemostat, in an illustrated embodiment, as shown in FIG. 1, FIG. 4, FIG. 5 and FIG. 6, a display screen 10 and keys 11 are disposed on the housing 1. Moreover, an integrated circuit board 12 and a battery 13 are disposed in the housing 1. The integrated circuit board 12 is disposed thereon a controller 14, an alarm loudspeaker 15, a clock chip 16, and a wireless charging coil 17. The gear motor 3, the pressure sensor 2, the display screen 10, the keys 11, the controller 14, the alarm loudspeaker 15, the clock chip 16, the wireless charging coil 17 and the battery 13 all are electrically connected to the integrated circuit board 12. The vibration sensors 8 and the far-infrared temperature sensors 9 are electrically connected to the integrated circuit board 12 through a flexible flat cable (FFC) 18. The flexible flat cable 18 is arranged penetrating through the pressing plate 5 and the compression rod 5 sequentially. The wireless charging coil 17 is configured to charge the battery 13.

In some embodiments, a control method of the radial artery smart compression hemostat may include steps as follows.

S1, recording a systolic blood pressure as Ps and a diastolic blood pressure as Pd of a patient obtained by preoperative measurement (i.e., measured before an operation).

S2, tying/binding the radial artery smart compression hemostat to a wrist 21 of the patient by using the bandage 7 after an operation, and a center location of the compression pad 6 being abutted against the radial artery puncture site.

S3, driving the compression rod 4, the pressing plate 5 and the compression pad 6 sequentially to move close to the radial artery puncture site through the gear motor 3, to make the compression pad 6 apply a pressure force F onto skin at the puncture site. The pressure force F is measured by the pressure sensor 2, and can be correspondingly converted into a pressure intensity P (mmHg). A high-pressure compression time is set as $\Delta T0$, a high-pressure relief time is set as $\Delta T1$, various stage compression times are set as $\Delta Tj$, and a total compression time is set as Tt, then $Tt=\Delta T0+\Delta T1+\Delta Tj*n$. These times are displayed on the display screen 10 through the clock chip 16. At the beginning of hemostasis, $P=Ps+Pa1$ and maintained for the time $\Delta T0$; then P gradually decreases at the rate of $Pa1/\Delta T1$ until $P=Ps$. Afterwards, P decreases gradually with the stage compression times $\Delta Tj$, $P=Ps-(Ps-Pd+Pa2)*j/n$, until $P=Pd-Pa2$, and correspondingly the hemostatic process is ended, where $j=1, 2, 3, \ldots, n$, n is an integer; Pa1 and Pa2 both are constants and each correspond to a threshold. Specifically, a value range of Pa1 is 0-30 mmHg, and the value of Pa1 is comprehensively determined by a use condition of anticoagulant, a condition of blood pressure and a condition of coagulation function of the patient; and a value range of Pa2 is 0-20 mmHg.

S4, prompting by the alarm loudspeaker to indicate that the radial artery smart compression hemostat needs to be removed from the wrist 21 of the patient, to thereby ensure that a medical staff ends the hemostasis operation for the patient in time.

In some embodiments, in the step S3, a pulse intensity at a proximal end and a pulse intensity at a distal end measured by the two vibration sensors 8 are respectively recorded as Ha1 and Ha2, and a pulse vibration amplitude difference coefficient is set as $ha=Ha2/Ha1$. If ha is close to 0 and the value of ha specifically is within a range of 0 to 0.2, indicating that the blood vessel is occluded and there is no blood flow at the distal end; whereas if ha is close to 1 and the value of ha specifically is within a range of 0.8 to 1, indicating that the blood vessel is unobstructed; that is, according to the pulse vibration amplitude difference between the pulse intensity at the proximal end and the pulse intensity at the distal end, the blood flow unobstructed (or occluded) condition at the distal end can be accurately determined. Meanwhile, a skin surface temperature at the puncture site measured by the far-infrared temperature sensors 9 is recorded as Temp, if there is no oozing of blood at the radial artery puncture site, the skin surface temperature at the puncture site is not higher than the body temperature, which is recorded as Temp0; if there is oozing of blood at the radial artery puncture site, the skin surface temperature at the puncture site rises; if the oozing of blood continues, the skin surface temperature at the puncture site will rise to close to the body temperature, which is recorded as Temps, and $Temp0 \leq Temp0 \leq Temps$.

In the whole hemostasis process, ha and Temp are monitored in real time, a blood vessel occlusion interval time is set as Tc, and a blood vessel release interval time is set as To; if a time length of ha close to 0 is greater than the time Tc, and specifically the time length of the value of ha being in the range of 0 to 0.2 is greater than the time Tc, the pressure is released until the value of ha is within a range of 0.45 to 0.55 and maintained for the time To, and the compression pad 6 then restores to the pressure before the releasing. If Temp rises abnormally at any time during the whole hemostasis process, for example, $Temp \geq Temps-0.5$, P returns to an immediately preceding pressure level and is maintained for $\Delta Tj$, alarms on the display screen 10 and records once. When current $\Delta Tj$ ends, it is determined whether $Temp \leq Temp0+0.5$ or not within a time period of $\alpha*\Delta Tj$ before the current moment; if yes, going to a next pressure stage; whereas if no, continuing maintaining the current pressure stage for the time period of $\alpha*\Delta Tj$. Where, $\alpha$ is a constant and corresponds to a threshold, and specifically a value range of $\alpha$ is, for example, 0-0.5, and the value of $\alpha$ in an illustrated embodiment is $\frac{1}{3}$. According to the difference of pulse vibration amplitudes returned by the two vibration sensors 8, the blood flow condition (i.e., patency or occlusion) at the distal end can be determined; according to the temperatures returned by the far-infrared temperature sensors 9, whether there is oozing of blood and a size of the oozing of blood can be determined; and then the pressure of the compression pad 6 applied on the radial artery puncture site can be adjusted in time, which can effectively avoid long-term compression ischemia at the distal end, effectively avoid oozing of blood cause by insufficient pressure, achieve the purpose of radial artery compression hemostasis as soon as possible under the condition of ensuring smooth blood flow of limbs to the greatest extent and no or less oozing of blood, and reduce secondary injury and sequelae after compression.

The foregoing description is merely preferred embodiments of the present disclosure, but the scope of protection of the present disclosure is not limited thereto. Any equivalent substitution or modification made by those skilled in the art according to the described technical solutions of the present disclosure and the inventive concept thereof within the technical scope illustrated by the present disclosure shall be included in the scope of protection of the present disclosure.

What is claimed is:

1. A radial artery smart compression hemostat, comprising: a housing (1), a pressure sensor (2), a gear motor (3), and a compression rod (4); wherein the pressure sensor (2) and the gear motor (3) both are disposed in the housing (1), a fixed end of the pressure sensor (2) is fixedly connected to the housing (1), the gear motor (3) is fixedly disposed on a measuring end of the pressure sensor (2), an output end of the gear motor (3) is threadedly connected to an end of the compression rod (4), a guiding channel (1-1) is disposed on the housing (1), the compression rod (4) is slidably disposed in the guiding channel (1-1), a pressing plate (5) is disposed on an end of the compression rod (4) facing away from the gear motor (3), the pressing plate (5) is exposed outside the housing (1), a silicone compression pad (6) is detachably sleeved on the pressing plate (5), a bandage (7) is disposed on the housing (1), the bandage (7) is configured to tie the radial artery smart compression hemostat to a wrist (21) of a patient and thereby the compression pad (6) is configured to be compressed on a radial artery puncture site.

2. The radial artery smart compression hemostat as claimed in claim 1, wherein the pressure sensor (2) is a stress-strain pressure sensor, a fixing plate (19) is disposed between the fixed end of the pressure sensor (2) and the housing (1), the fixed end of the pressure sensor (2) and the housing (1) are fixedly connected to the fixing plate (19) through screws, and the gear motor (3) is fixedly disposed on the measuring end of the pressure sensor (2) through a connecting piece.

3. A control method of the radial artery smart compression hemostat as claimed in claim 1, comprising steps of:

S1, recording a systolic blood pressure as Ps and a diastolic blood pressure as Pd of the patient measured before an operation;

S2, tying the radial artery smart compression hemostat to a wrist (21) of the patient through the bandage (7) after the operation, wherein a center location of the compression pad (6) abuts against the radial artery puncture site; and S3, driving the compression rod (4), the pressing plate (5) and the compression pad (6) sequentially through the gear motor (3) to move close to the radial artery puncture site, thereby making the compression pad (6) apply a pressure force F to skin at the radial artery puncture site;

converting the pressure force F into a pressure intensity P correspondingly; setting a high-pressure compression time $\Delta T0$, a high-pressure relief time $\Delta T1$, various stage compression times $\Delta Tj$, and a total compression time Tt, where $Tt=\Delta T0+\Delta T1+\Delta Tj*n$; wherein at a beginning of hemostasis, $P=Ps+Pa1$ and lasts for $\Delta T0$; P then gradually decreases at a rate of $Pa1/\Delta T1$, until $P=Ps$; and afterwards, P decreases gradually with the stage compression times $\Delta Tj$, $P=Ps-(Ps-Pd+Pa2)*j/n$, until $P=Pd-Pa2$, and a process of hemostasis is ended; where Pa1 and Pa2 both are constants and each correspond to a threshold, $j=1, 2, 3, \ldots, n$, and n is an integer.

4. The control method as claimed in claim 3, wherein the pressing plate (5) is rectangular, and a lengthwise direction of the pressing plate (5) is orientated along a blood vessel direction of a radial artery; two vibration sensors (8) are disposed on the pressing plate (5), and the two vibration sensors (8) are respectively arranged on a proximal end and a distal end of the radial artery puncture site; and far-infrared temperature sensors (9) are disposed on the pressing plate (5) and arranged along the lengthwise direction of the pressing plate (5), and the far-infrared temperature sensors (9) are located between the two vibration sensors (8);

wherein the S3 comprises: recording a pulse intensity at the proximal end as Ha1 and a pulse intensity at the distal end as Ha2 measured by the two vibration sensors (8) respectively; setting a pulse vibration amplitude difference coefficient as ha-Ha2/Ha1, wherein a value of ha in a range of 0 to 02 indicates a blood vessel is occluded and there is no blood flow at the distal end, and the value of ha in a range of 0.8 to 1 indicates the blood vessel is unobstructed; recording a skin surface temperature at the radial artery puncture site measured by the far-infrared temperature sensors (9) as Temp, recording the skin surface temperature at the radial artery puncture site as Temp0 when there is no oozing of blood at the radial artery puncture site, and recording the skin surface temperature at the radial artery puncture site as Temps after rises resulting from continuous oozing of blood when there is oozing of blood at the radial artery puncture site which causes the skin surface temperature at the radial artery puncture site rises, where $Temp0\leq Temp\leq Temps$;

wherein the control method comprises: in a whole process of hemostasis, monitoring ha and Temp in real time; setting a blood vessel occlusion interval time Tc and a blood vessel release interval time To; releasing the pressure intensity P until the value of ha is in a range of 0.45 to 0.55 when a time length of the value of ha being in the range of 0 to 0.2 is greater than the time Tc and maintaining for the time To, and then the compression pad (6) restoring to the pressure intensity P before the releasing; making the pressure intensity P return to immediately preceding pressure level and then be maintained for $\Delta Tj$ when Temp rises abnormally at any time during the whole process of hemostasis, determining whether $Temp\leq Temp0+0.5$ or not within a time period of $\alpha*\Delta Tj$ before current moment when current $\Delta Tj$ ends, going to a next pressure stage if $Temp\leq Temp0+0.5$, whereas if $Temp\leq Temp0+0.5$ is not satisfied, continuing maintaining current pressure stage for a time period of $\alpha*\Delta Tj$, where $\alpha$ is a constant and corresponds to a threshold.

5. The control method as claimed in claim 3, wherein a value range of Pa1 is 0 to 30 mmHg, a value range of Pa2 is 0 to 20 mmHg, and a value range of a is 0 to 0.5.

6. The control method as claimed in claim 3, wherein the radial artery smart compression hemostat is disposed with an alarm loudspeaker (15), and the control method further comprises:

S4, promoting by the alarm loudspeaker (15), to indicate that the radial artery smart compression hemostat needs to be removed from the wrist (21) of the patient.

7. The radial artery smart compression hemostat as claimed claim 1, wherein the pressing plate (5) is rectangular, and a lengthwise direction of the pressing plate (5) is oriented along a blood vessel direction of a radial artery.

8. The radial artery smart compression hemostat as claimed in claim 7, wherein two vibration sensors (8) are disposed on the pressing plate (5), and the two vibration sensors (8) are respectively arranged on a proximal end and a distal end of the radial artery puncture site.

9. The radial artery smart compression hemostat as claimed in claim 8, wherein far-infrared temperature sensors (9) are disposed on the pressing plate (5) and arranged along the lengthwise direction of the pressing plate (5), and the far-infrared temperature sensors (9) are located between the two vibration sensors (8).

10. The radial artery smart compression hemostat as claimed in claim 9, wherein a display screen (10) and keys (11) are disposed on the housing (1), an integrated circuit board (12) and a battery (13) are disposed in the housing (1); the integrated circuit board (12) is disposed thereon a controller (14), an alarm loudspeaker (15), a clock chip (16), and wireless charging coil (17); the gear motor (3), the pressure sensor (2), the display screen (10), the keys (11), the controller (14), the alarm loudspeaker (15), the clock chip (16), the wireless charging coil (17) and the battery (13) all are electrically connected to the integrated circuit board (12); the two vibration sensors (8) and the far-infrared temperature sensors (9) are electrically connected to the integrated circuit board (12) through a flexible flat cable (18); the flexible flat cable (18) is arranged passing through the pressing plate (5) and the compression rod (4) sequentially; and the wireless charging coil (17) is configured to charge the battery (13).

* * * * *